(12) United States Patent
Muir

(10) Patent No.: US 10,933,418 B2
(45) Date of Patent: Mar. 2, 2021

(54) BIOLOGICAL ANALYSIS APPARATUS

(71) Applicant: CYTOMOS LIMITED, Edinburgh Lothian (GB)

(72) Inventor: Keith Muir, Edinburgh (GB)

(73) Assignee: CYTOMOS LIMITED, Edinburgh (GB)

( * ) Notice: Subject to any disclaimer, the term of this patent is extended or adjusted under 35 U.S.C. 154(b) by 0 days.

(21) Appl. No.: 14/902,283

(22) PCT Filed: Jul. 4, 2014

(86) PCT No.: PCT/GB2014/052044
§ 371 (c)(1),
(2) Date: Dec. 30, 2015

(87) PCT Pub. No.: WO2015/001355
PCT Pub. Date: Jan. 8, 2015

(65) Prior Publication Data
US 2016/0370278 A1  Dec. 22, 2016

(30) Foreign Application Priority Data
Jul. 4, 2013  (GB) .................................. 1312035.7

(51) Int. Cl.
*B01L 3/00* (2006.01)
*G01N 33/48* (2006.01)
(Continued)

(52) U.S. Cl.
CPC ... *B01L 3/502761* (2013.01); *B01L 3/502776* (2013.01); *G01N 15/0266* (2013.01);
(Continued)

(58) Field of Classification Search
USPC ...................................... 422/502–504, 82.01
See application file for complete search history.

(56) References Cited

U.S. PATENT DOCUMENTS 5,370,842 A   12/1994  Miyazaki et al.
6,294,063 B1 *  9/2001  Becker ................ B01F 13/0076
                                                    204/450
(Continued)

FOREIGN PATENT DOCUMENTS

EP      0246011      11/1987
EP      1528387       5/2005
(Continued)

OTHER PUBLICATIONS

Linder et al, "Microfluidics/CMOS Orthogonal Capabilities for Cell Biology", Biomed Microdevices, Springer Science + Business Media (2006) 8: pp. 159-166.
(Continued)

*Primary Examiner* — Dean Kwak
(74) *Attorney, Agent, or Firm* — Liu & Liu

(57) ABSTRACT

The present invention relates to biological sensing apparatus (12) which is configured to sense particles comprised in fluent material. The biological sensing apparatus (12) comprises particle sensing apparatus (32) comprised in an integrated circuit formed by a semiconductor fabrication process, the particle sensing apparatus being configured to sense an electrical property. The biological sensing apparatus further comprises a flow arrangement 30 configured to contain and provide for flow of fluent material. The particle sensing apparatus (32) is disposed relative to the flow arrangement (30) such that the particle sensing apparatus is operative to sense an electrical property of particles comprised in the fluent material as the fluent material flows through the flow arrangement.

17 Claims, 3 Drawing Sheets

(51) Int. Cl.
  *G01N 15/10* (2006.01)
  *G01N 15/02* (2006.01)
  *G01N 33/49* (2006.01)
  *G01N 15/00* (2006.01)

(52) U.S. Cl.
  CPC ..... *G01N 15/1031* (2013.01); *G01N 15/1056* (2013.01); *G01N 33/48* (2013.01); *B01L 2300/0645* (2013.01); *B01L 2300/0816* (2013.01); *B01L 2300/0864* (2013.01); *B01L 2300/0867* (2013.01); *G01N 33/49* (2013.01); *G01N 2015/0065* (2013.01); *G01N 2015/1006* (2013.01)

(56) References Cited

U.S. PATENT DOCUMENTS

| | | | |
|---|---|---|---|
| 6,437,551 | B1 | 8/2002 | Krulevitch et al. |
| 8,689,981 | B2* | 4/2014 | Stone ............... B03C 1/288 209/214 |
| 2009/0032401 | A1* | 2/2009 | Ronaghi ........... B01L 3/502761 204/549 |
| 2010/0000404 | A1 | 1/2010 | Sakuma et al. |
| 2016/0296944 | A1* | 10/2016 | Koser ............... B03C 1/0332 |

FOREIGN PATENT DOCUMENTS

| | | |
|---|---|---|
| JP | H05240872 | 9/1993 |
| JP | 2010008332 | 1/2010 |
| JP | 2012-141263 A | 7/2012 |
| WO | 00/63407 | 10/2000 |
| WO | 00/63408 | 10/2000 |
| WO | 01/18246 | 3/2001 |
| WO | 2005/099419 | 10/2005 |
| WO | 2008/111677 | 9/2008 |
| WO | 2008/112635 | 9/2008 |
| WO | 2009/053907 | 4/2009 |
| WO | 2012/054904 | 4/2012 |

OTHER PUBLICATIONS

Hunt et al., "Integrated Circuit/Microfluidic Chip to Programmably Trap and Move Cells and Droplets with Dielectrophoresis", The Royal Society of Chemistry, Lab on a Chip (Jan. 2008), vol. 8, No. 1, pp. 81-87.
Romani et al., "Capacitive Sensor Array for Localization of Bioparticles in CMOS Lab-on-a-Chip", IEEE International Solid-State Circuits Conference (2004), Session 12, Biomicrosystems, 12.4, pp. 1-8.
Sun et al., "Digital Signal Processing Methods for Impedance Microfluidic Cytometry", Microfluid Nanofluid, Springer-Verlag (2008), pp. 1-9.
Cheung et al., "Impedance Spectroscopy Flow Cytometry: On-Chip Label-Free Cell Differentiation", Cytometry Part A, Wiley-Liss (2005), 65A, pp. 124-132.
Gawad et al., "Micromachined Impedance Spectroscopy Flow Cytometer for Cell Analysis and Particle Sizing", The Royal Society of Chemistry, Lab on a Chip (2001), vol. 1, pp. 76-82.

* cited by examiner

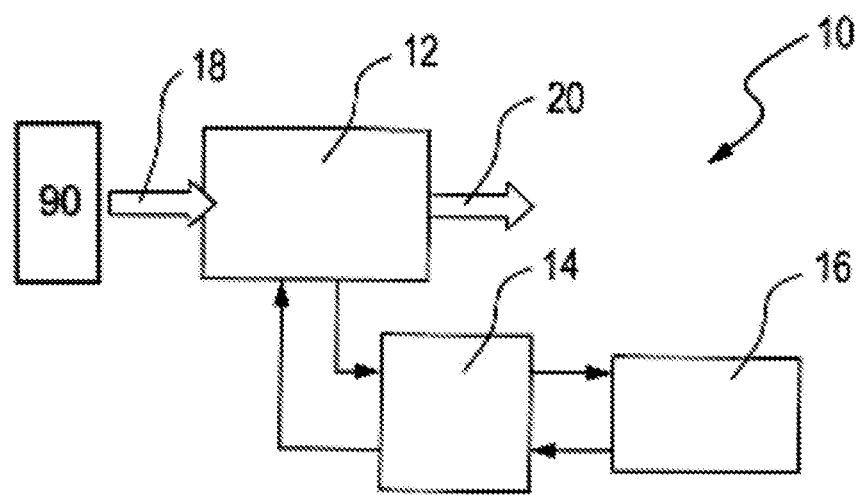
_Fig. 1_
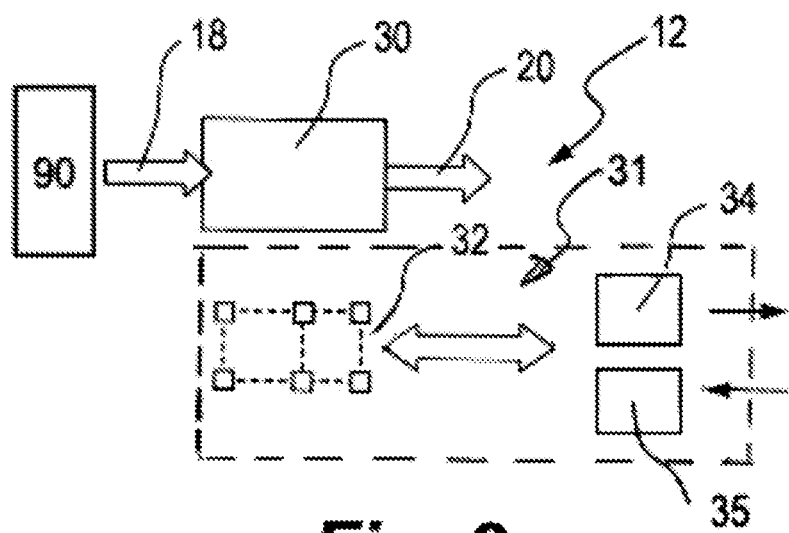
_Fig. 2_

BIOLOGICAL ANALYSIS APPARATUS

FIELD OF THE INVENTION

The present invention relates to sensing apparatus for sensing particles, such as biological cells, in fluent material, a method therefor and analysis apparatus comprising such sensing apparatus.

BACKGROUND ART

The analysis of physical or chemical characteristics of biological particles finds use in the diagnosis of disease, in research, in clinical trials of drugs and the like. It is known to employ apparatus to carry out such analysis on an automatic basis with the apparatus being configured to provide for simultaneous multi-parametric analysis of many particles per second. Typically the biological particles of interest are suspended in a fluid before being introduced to the analysis apparatus where the suspended biological particles are subject to excitation and the response to the excitation is detected. A known approach to analysis involves introducing a fluorochrome to the biological particle suspension and then directing a beam of light onto the biological particle suspension. According to this known approach light scattered by the biological particle suspension and light re-emitted from the biological particle suspension on account of the fluorochrome are detected and analytical determinations are made in dependence on the detected light.

The present inventor has become appreciative of shortcomings in known approaches to the analysis of biological particles. More specifically and amongst other things the present inventor has become appreciative of the large size of known biological particle analysis apparatus.

It is therefore an object for the present invention to provide biological sensing apparatus for sensing particles comprised in fluent material, the biological sensing apparatus being configured to provide for portability and perhaps also for hand portability.

It is a further object for the present invention to provide a biological sensing method for sensing particles comprised in fluent material, the method being accomplished within portable apparatus and perhaps also within hand portable apparatus.

STATEMENT OF INVENTION

According to a first aspect of the present invention there is provided biological sensing apparatus configured to sense particles comprised in fluent material, the biological sensing apparatus comprising:
  particle sensing apparatus comprised in an integrated circuit formed by a semiconductor fabrication process, the particle sensing apparatus being configured to sense an electrical property; and
  a flow arrangement configured to contain and provide for flow of fluent material,
  the particle sensing apparatus being disposed relative to the flow arrangement such that the particle sensing apparatus is operative to sense an electrical property of particles comprised in the fluent material as the fluent material flows through the flow arrangement.

In use a sample of fluent material, such as a biological sample, is introduced into the flow arrangement with the flow arrangement being configured to contain and provide for flow of the fluent material. The flow arrangement may be configured to contain the fluent material so as to provide for flow of the fluent material. The flow arrangement may, for example, define an open ended channel which contains the fluent material and allows for flow such as when flow is created by way of a pump. Alternatively or in addition, the flow arrangement may be configured to actuate flow of itself. More specifically the flow arrangement may be configured to draw the fluent material through the flow arrangement by way of capillary action. The particle sensing apparatus is comprised in an integrated circuit formed by a semiconductor fabrication process, such as a CMOS fabrication process. The particle sensing apparatus is configured to sense an electrical property. The particle sensing apparatus is disposed relative to the flow arrangement such that the particle sensing apparatus is operative to sense an electrical property of particles comprised in the fluent material as the fluent material flows through the flow arrangement. The particles may be biological particles, e.g. cells or other structures including viruses, multi-cell organisms, bacteria and spores. Sensing of particles may provide for analysis of the particles involving, for example, differentiation of cell species from each or one another.

The particle sensing apparatus may be configured to sense a quantity corresponding to electrical permittivity of a particle. The particle sensing apparatus may be configured to sense a quantity corresponding to at least one of real and imaginary electrical permittivity of a particle. More specifically the particle sensing apparatus may be configured to sense electrical permittivity of a particle. As described further below, the particle sensing apparatus may therefore be configured to sense an electric field present in the fluent material. The particle sensing apparatus may be configured to sense a response to a stimulus applied to the fluent material. A particle, such as a cell, may cooperate with the applied stimulus in a characteristic fashion so as to provide a response that may be sensed. The particle sensing apparatus may therefore be used to sense the presence of a particle in the fluent material. Furthermore different particles may cooperate with the applied stimulus in different characteristic fashions so as to provide corresponding different responses.

The particle sensing apparatus may therefore be used to characterise a particle. For example the particle sensing apparatus may be used to at least one of differentiate one type of cell from another type of cell and determine a characteristic of a cell, such as a dimension of the cell or a composition of a cell.

A stimulus which may be applied to the fluent material may comprise an electric field. A stimulus in the form of an electric field may be appropriate for sensing certain cells, such as biological cells. Furthermore electrical sensors may be readily provided in an integrated circuit formed by a semiconductor fabrication process and in particular so as to provide for particle sensing apparatus dimensions which correspond in size to certain forms of particle, such as biological cells.

According to an embodiment the particle sensing apparatus may be configured to sense an electric field present in the fluent material. A particle, such as a cell, may cooperate with such an electric field whereby the electric field is disturbed. The particle sensing apparatus may therefore be used to sense the presence of a particle in the fluent material in dependence on disturbance of the electric field. Furthermore different particles may disturb an electric field in a different fashion. The particle sensing apparatus may therefore be used to characterise a particle. For example the particle sensing apparatus may be used to differentiate one type of cell from another type of cell. In certain forms of the embodiment the fluent material may comprise at least one electrically sensitive label. The presence of an electrically sensitive label may provide for an improved response or enhanced capability. Such forms may be configured to be operative upon changes to the electric field caused by the use of electrically sensitive labels or to make use of the response provided by the electrically sensitive labels.

The particle sensing apparatus may comprise a sensing arrangement disposed relative to the flow arrangement whereby, in use, the sensing arrangement is operative to sense an electric field present in fluent material. The sensing arrangement may comprise at least one electrode pair. A pair of electrodes may be disposed relative to each other and relative to fluent material in the flow arrangement so as to sense an electric field present in the fluent material. One of the pair of electrodes may be disposed on or towards a side of the fluent material, such as in a direction perpendicular to a direction of flow of the fluent material. The other of the pair of electrodes may be disposed on or towards a side of the fluent material. The pair of electrodes may be disposed on or towards substantially a same side of the fluent material. The pair of electrodes may be disposed side by side. Such a same side disposition may be appropriate where the particle sensing apparatus is comprised in a planar semiconductor integrated circuit, such as a CMOS integrated circuit. An electrode may have a dimension, such as at least one of width and height, of less than substantially 100 microns, 50 microns, 30 microns, 20 microns, 15 microns, 10 microns, 5 microns, 3 microns or 1 micron. Alternatively or in addition an electrode may have a dimension of more than substantially 0.5 microns, 1 micron, 5 microns, 10 microns, 15 microns, 20 microns, 30 microns or 50 microns.

The particle sensing apparatus may comprise plural spaced apart sensing arrangements, e.g. plural electrode pairs, with each sensing arrangement being operative to sense particles. Furthermore the flow arrangement may define a flow path along which a particle travels and the particle sensing apparatus may be configured such that as a particle travels along the flow path the particle is sensed by successive sensing arrangements.

The particle sensing apparatus may further comprise a sensing circuit configured to receive an input signal from the sensing arrangement and to provide a corresponding output signal. The sensing circuit may be configured to sense charge, such as may be present on an electrode. More specifically the sensing circuit may comprise a capacitor which is operative to sense charge and to convert the sensed charge to a voltage signal. The sensing circuit may comprise a high impedance input to thereby provide for a significant sensed signal. More specifically the sensing circuit may comprise an impedance buffer, such as a field-effect transistor (FET). A FET may provide a capacitive load, e.g. for an electrode of the particle sensing apparatus. Alternatively or in addition the sensing circuit may provide one of a voltage signal and a current signal as the output signal. Alternatively or in addition the sensing circuit may be configured to amplify the input signal. For example the sensing circuit may be configured to convert electrical charge present on an electrode: to a corresponding voltage and to amplify the converted voltage; or to a corresponding current and to amplify the converted current.

Use of an electrostatic field as the stimulus may be appropriate in certain applications. The particle sensing apparatus may therefore be configured to sense an electrostatic field. Use of an electrodynamic field may be appropriate in certain other applications. For example and where the particles comprise biological cells the application of an electrostatic field may compromise characterisation of the biological cells on account of an adverse electrochemical response to the electric field by the biological cells and fluent material and may perhaps result in damage to the biological cells if the electric field is of high intensity. The particle sensing apparatus may therefore be configured to sense an electrodynamic field. An electrodynamic field may be less liable to cause an adverse electrochemical response in biological cells. For example and where the particle sensing apparatus comprises a sensing circuit the sensing circuit may be configured to have sufficient bandwidth to operate upon varying signals sensed in respect of the electrodynamic field.

The biological sensing apparatus may further comprise stimulation apparatus which is configured to, in use, stimulate particles comprised in the fluent material. Stimulation of the particles may cause the particles to respond in a fashion susceptible to sensing, such as by the particle sensing apparatus described above. The biological sensing apparatus may be configured such that the stimulation apparatus and the particle sensing apparatus are operative simultaneously. More specifically the biological sensing apparatus may be configured such that the particle sensing apparatus is operative to sense particles comprised in the fluent material at the same time as the stimulation apparatus is operative to stimulate particles comprised in the fluent material.

According to a second approach, the stimulation apparatus may be configured to apply an electric field to the fluent material. The application of an electric field to the fluent material may, in certain circumstances, provide for a response from the particles of themselves, e.g. without the use of labels to accentuate the response to the stimulus. As mentioned above, stimulation apparatus configured to apply an electric field may be more readily formed with a semiconductor fabrication process, such as CMOS. The electric field source may therefore be comprised in the integrated circuit comprising the particle sensing apparatus. Furthermore formation of the electric field source with a semiconductor fabrication process may provide for dimensions of the electric field source which correspond in size to certain forms of particle, such as biological cells. Where the fluent material comprises at least one electrically sensitive label the stimulation apparatus may be configured appropriately.

The electric field source may be configured to apply an electric field to the fluent material. As mentioned above the application to the fluent material of an electrodynamic field may be preferred over an electrostatic field in certain applications. The electric field source may therefore comprise a voltage source which is operative to generate a voltage signal and more specifically a varying voltage signal to thereby provide for application of the electric field. The electric field source may be configured such that the voltage source applies the voltage signal to electrodes as described below, the electrodes being disposed relative to the flow arrangement such that an electric field is applied to fluent material in the flow arrangement.

The biological sensing apparatus may be configured such that at least one of a stimulation element and a sensing element may be substantially electrically isolated from fluent material in the flow arrangement. Such electrical isolation may significantly reduce charge flow in the fluent material, e.g. upon application of a stimulus in the form of a varying electric field. Reduction in charge flow in the fluent material may maintain the integrity of particles comprised in the fluent material and may also provide for integrity of measurement. Electrical isolation may be achieved by an isolating arrangement disposed, for example, between a stimulation element or a sensing element and a fluent material containing part of the flow arrangement. According to one approach the isolating arrangement may be constituted by a dielectric layer comprised in the integrated circuit. More specifically the dielectric layer may comprise a passivation layer, such as of silicon nitride. According to another approach the isolating arrangement may comprise a polymer and more specifically a thermoplastic fluoropolymer, such as polyvinylidene fluoride (PVDF). Particles comprised in the fluent material, such as biological cells, have been found to be less liable to stick to the like of PVDF than a passivation layer.

The stimulation apparatus may comprise a stimulation arrangement disposed relative to the flow arrangement whereby, in use, the stimulation arrangement is operative to apply an electric field to the fluent material. The stimulation arrangement may comprise at least one electrode pair. A pair of electrodes may be disposed relative to each other and relative to fluent material in the flow arrangement so as to apply an electric field to the fluent material. One of the pair of electrodes may be disposed on or towards a side of the fluent material, such as in a direction perpendicular to a direction of flow of the fluent material. The other of the pair of electrodes may be disposed on or towards a side of the fluent material. The pair of electrodes may be disposed on or towards substantially a same side of the fluent material. The pair of electrodes may be disposed side by side. Such a same side disposition may be appropriate where the particle stimulation apparatus is comprised in a planar semiconductor integrated circuit, such as a CMOS integrated circuit.

Where the particle sensing apparatus comprises a sensing arrangement comprising an electrode pair, at least one electrode of the electrode pair of the sensing arrangement may not be comprised in the electrode pair of the stimulation arrangement. The biological sensing apparatus may thus be configured to provide for effective simultaneous stimulation and sensing of particles in the fluent material. More specifically and in a first form the electrode pair of the stimulation arrangement and the electrode pair of the sensing arrangement may have an electrode in common. The first form may be appropriate for a single ended sensing approach. The sensing arrangement may therefore be a single ended sensing arrangement. In a second form the electrode pair of the stimulation arrangement and the electrode pair of the sensing arrangement may have no electrodes in common. The second form may be appropriate for a differential sensing approach. The sensing arrangement may therefore be a differential sensing arrangement. A differential sensing arrangement has been found to be less sensitive to variations in the fluent material and more specifically a medium comprising the particles being sensed. In addition a differential sensing approach provides for reduction in common mode signals. Reduction in common mode signals may be advantageous where the stimulus is a common mode signal and the response is single ended. The second form may also be appropriate for differential stimulation. The stimulation arrangement may therefore be a differential stimulation arrangement. A differential stimulation arrangement may provide for the application to the fluent material of a more significant stimulation signal than can be achieved with a single ended stimulation arrangement.

The biological sensing apparatus may be configured to apply a predetermined stimulation signal to the fluent material, e.g. by way of the stimulation apparatus. The biological sensing apparatus may be configured to compare the predetermined stimulation signal with a response to the stimulation signal, e.g. as sensed by the particle sensing apparatus. Comparison of the predetermined stimulation signal with the response may comprise cross-correlation of the predetermined stimulation signal with the response. The biological sensing apparatus may be operative to determine a time delay between application of the predetermined stimulation signal and the response as provided by at least one particle in the fluent material. The biological sensing apparatus may be further operative to determine a transfer function or at least to approximate a transfer function for the at least one particle in dependence on the time delay. The determined or approximated transfer function may then provide for characterisation of the at least one particle.

The predetermined signal may comprise a pseudo-random noise signal. The biological sensing apparatus may be configured to generate the pseudo-random noise signal. The pseudo-random noise signal may comprise an m-sequence. M-sequences exhibit a flat power spectral density across a desired bandwidth of operation. Furthermore m-sequences may be readily provided for by way of standard digital circuitry and thus may be suited to implementation in an integrated circuit formed by a semiconductor fabrication process, such as CMOS.

The biological sensing apparatus may be configured to sense a frequency component comprised in a signal, such as a varying electric field, sensed by the particle sensing apparatus, the frequency component being at least 1 kHz, 10 kHz, 50 kHz, 100 kHz, 250 kHz, 500 kHz, 1 MHz, 5 MHz, 10 MHz, 25 MHz, 50 MHz, 75 MHz, 100 MHz, 250 MHz, 500 MHz, 750 MHz, 1 GHz, 1.25 GHz, 1.5 GHz, 1.75 GHz, 2 GHz. 2.5 GHz, 2.75 GHz or 5 GHz. More specifically the frequency component may be between 10 kHz and 100 MHz. Under certain circumstances at a frequency above 1 MHz the particle sensing apparatus may be operative to characterise an inside of the at least one particle, such as where the at least one particle is a biological cell. Under certain circumstances a frequency above 1 kHz may be required to characterise a particle in respect of its external characteristics, such as a size of a biological cell. The power of a signal applied by the biological sensing apparatus, such as by way of the stimulation apparatus, may be at least 1 µW, 5 µW, 10 µW, 25 µW, 50 µW, 100 µW, 250 µW or 500 µW. Stimulation apparatus comprised in the biological sensing apparatus may therefore be configured to apply a stimulation signal, such as an electric field, comprising at least one corresponding frequency component. Where the particle sensing apparatus comprises a large number of stimulation and sensing elements, such as a large array of electrodes, which are addressed at high frequency, the addressing period for each stimulation element or sensing element may be shorter than the time required for stimulation or sensing. The biological sensing apparatus may therefore be configured to provide for persistence of at least one of a stimulation signal and particle sensing. More specifically the biological sensing apparatus may comprise a persistence circuit, such as electronic memory, which is configured to be addressed, e.g. in respect of each of plural stimulation elements, for a predetermined period and to hold a state for longer than the predetermined period. The persistence circuit may be configured to provide for application of a stimulation signal to a stimulation element over a period of time longer than the predetermined addressing period. Where the persistence circuit comprises electronic memory, the electronic memory may comprise at least one of Static Random Access Memory (SRAM) and Dynamic Random Access Memory (DRAM). Each of plural outputs from the persistence circuit may be electrically coupled to a respective one of plural stimulation elements.

Where the biological sensing apparatus comprises plural pairs of electrodes the biological sensing apparatus may be configured to change which electrodes are operative to apply a stimulus to the particles and which electrodes are operative to sense a response to the applied stimulus. The biological sensing apparatus may be configured to apply a stimulus with a first set of electrodes and sense a response with a second set of electrodes and then to apply a stimulus with the second set of electrodes and to sense a response with a third set of electrodes. Such an approach may be appropriate where the electrodes are disposed in a line, such as a line along which particles progress as they flow through the flow arrangement.

The particle sensing apparatus of the biological sensing apparatus may comprise an array of sensing elements, such as an array of electrodes as described elsewhere herein. The array may extend in a direction of flow of fluent material as provided by the flow arrangement. A particle may therefore be sensed by a succession of sensing elements as the particle progresses through the flow arrangement. Alternatively or in addition the array may extend in a direction perpendicular to a direction of flow of fluent material through flow arrangement. More specifically the array may extend in the direction of flow and perpendicular to the direction of flow whereby the array is a two dimensional array. An array of sensing elements may provide for simultaneous sensing operations, e.g. sensing and perhaps also stimulation of plural different particles at the same time. Sensing of plural different particles at the same time may comprise the application of plural stimuli at the same time. Alternatively or in addition an array may provide for actuation of particles as described below.

The biological sensing apparatus may comprise an array of actuating elements which extend in a direction perpendicular to a direction of flow of fluent material through the flow arrangement, the array of actuating elements being disposed relative to the flow arrangement so as to impart a force on a particle in the flow arrangement. The force may have a component which is in a direction perpendicular to the direction of flow to thereby move the particle in a direction other than the direction of flow.

The biological sensing apparatus may comprise an array of actuating elements which in turn comprises electrodes whereby the electrodes are in the form of an array. The biological sensing apparatus may be configured such that at least one set of electrodes in the array is operable to provide for at least one of actuation, stimulation and sensing. For example electrodes of the array may be used at one time for actuation, at another time for stimulation and at yet another time for sensing. The biological sensing apparatus may be configured to apply an actuating signal to plural actuating elements disposed in a direction other than a direction of flow of fluent material. The actuating signal may be applied to the plural actuating elements with at least one of different amplitude and different phase. Application of an actuating signal with at least one of different amplitude and different phase to different actuating elements may impart an actuating force on a particle. Actuation may be used to manipulate or sort particles. More specifically actuation may be used to move a particle or a group of particles to a desired part of the array, such as a part of the array having stimulation and sensing electrodes of a size corresponding to the size of the particle or particles, or to move different particles to different parts of the array before sensing takes place so that sensing may be carried out on plural particles at the same time by the different parts of the array.

The biological sensing apparatus may be operative and perhaps also configured to be label free. The biological sensing apparatus may therefore operate on fluent material lacking any label, such as a fluorochrome or microbeads.

The biological sensing apparatus may be operative and perhaps also configured for sensing of microbiological samples. The biological sensing apparatus may therefore be configured to sense particles, such as biological elements, which have a dimension of less than substantially 500 microns, 250 microns, 200 microns, 150 microns, 100 microns, 50 microns, 25 microns, 10 microns, 5 microns, 2 microns, 1 micron, 500 nm, 250 nm, 100 nm, 50 nm, 25 nm, 10 nm or 5 nm. Alternatively or in addition the biological sensing apparatus may be configured to sense particles which have a dimension greater than substantially 2 nm, 5 nm, 10 nm, 25 nm, 50 nm, 100 nm, 250 nm, 0.5 microns, 1 micron, 2 microns, 5 microns, 10 microns, 25 microns, 50 microns, 100 microns, 150 microns, 200 microns or 250 microns. The biological sensing apparatus may be configured for a particular size of particle or a range of sizes of particles in respect of a dimension of at least one of a stimulation arrangement and a sensing arrangement, such as a size of at least one electrode. More specifically a dimension of at least one of a stimulation arrangement and a sensing arrangement may correspond to a size of particle or a range of sizes of particles. Formation of at least one of the sensing arrangement and the stimulation arrangement by way of a semiconductor fabrication process may provide for their scaling to enable at least one of sensing and stimulation of particles of a particular size or range of sizes.

The semiconductor fabrication process may be a planar semiconductor fabrication process. Alternatively or in addition the semiconductor fabrication process may be a metal-oxide semiconductor process, such as a CMOS process. Alternatively or in addition the semiconductor fabrication process may be a submicron semiconductor fabrication process, such as a 0.35 micron CMOS process and perhaps a high voltage 0.35 micron CMOS process.

The fluent material may be substantially liquid, e.g. at room temperature. The fluent material may therefore comprise a liquid which carries the particles. More specifically the fluent material may comprise charge carriers, such as salt molecules. For example the fluent material may comprise phosphate buffered saline (PBS).

The flow arrangement may define a main channel through which the fluent material flows when in use. The particle sensing apparatus may be disposed relative to the main channel so as to provide for sensing of particles present in the main channel. The particle sensing apparatus may be disposed on at least one of first and second opposite sides of a flow of fluent material. Thus, for example, components such as electrodes of the particle sensing apparatus may be disposed on one side of the flow of fluent material. According to another example, components of the particle sensing apparatus may be disposed on both sides of the flow of fluent material. The flow arrangement may comprise a sample inlet which is configured to receive a sample of fluent material, e.g. by way of injection, which is to be subject to sensing, the sample inlet being in fluid communication with the main channel. The flow arrangement may comprise a sample outlet at an opposite end of the flow arrangement from the sample inlet, the sample outlet being in fluid communication with the main channel.

The sample outlet may provide for flow of fluent material from the main channel. The flow arrangement may comprise at least one further inlet disposed laterally of the sample inlet. More specifically the flow arrangement may comprise first and second further inlets with the first inlet disposed laterally on one side of the sample inlet and the second inlet disposed laterally on another opposite side of the sample inlet. The at least one further inlet may be in fluid communication with the main channel. In use a sheath fluid, such as phosphate buffered saline (PBS), may be received by the at least one further inlet to thereby provide for a flow of sheath fluid in the main channel, the flow of sheath fluid being lateral of a flow of fluent material. The flow of sheath fluid may provide for registration of the particle comprising fluent material with the particle sensing apparatus and may also help preserve the integrity of the flow of fluent material as it progresses though the flow arrangement. The flow arrangement may comprise at least one further outlet disposed at an opposite end of the flow arrangement from the at least one further inlet, the at least one further outlet being in fluid communication with the main channel. The at least one further outlet may provide for flow of sheath fluid from the main channel.

The flow arrangement may be formed at least in part from a polymer, such as poly(methyl methacrylate) (PMMA). The flow arrangement may be of a length of substantially 25 mm and of a width of substantially 10 mm. The particle sensing apparatus and the flow arrangement may be separately formed. The particle sensing apparatus may be disposed relative to the flow arrangement by attaching the particle sensing apparatus and the flow arrangement to each other. The particle sensing apparatus and the flow arrangement may be releasably attached to each other, e.g. by way of a fastener arrangement comprising a silicone gasket layer. Releasable attachment may provide for ease of replacement of the flow arrangement, e.g. where the flow arrangement has reached its end of life or where a differently configured flow arrangement is required.

The biological sensing apparatus may be further configured to sense at least one of: a light permittivity; and a light permeability. As described further below, the particle sensing apparatus may therefore be further configured to sense light emitted by the fluent material. The particle sensing apparatus may thus be configured to sense light emitted by the fluent material in addition to sensing an electrical property of the fluent material. The particle sensing apparatus may be further configured to sense light emitted by the fluent material. The emitted light may be light transmitted through or reflected, e.g. scattered, by the fluent material in dependence on application of light to the fluent material. Alternatively the emitted light may be light re-emitted by a fluorochrome comprised in the fluent material, the fluorochrome being operative to re-emit light in dependence on light impinging on the fluent material. The particle sensing apparatus may therefore further comprise a light sensor which is disposed relative to the flow arrangement such that the light sensor is operative to sense light emitted by the fluent material. More specifically the particle sensing apparatus may comprise a light sensitive electrical circuit. The light sensitive electrical circuit may be of a form suitable for formation by a semiconductor fabrication process, such as a CMOS process. The light sensitive electrical circuit may therefore comprise a photosensitive junction and more specifically a metallurgical photosensitive junction, such as a photodiode (PD). A photodiode typically occupies little area in an integrated circuit and may therefore be readily incorporated into a relatively dense electrode array, such as the electrode array described below.

Stimuli applied to the fluent material may further comprise electromagnetic radiation. The stimuli may comprise light and more specifically visible light. A stimulus comprising visible light has been found appropriate for certain forms of particle, such as biological cells. The stimulation apparatus may be configured to apply electromagnetic radiation, such as light and more specifically visible light, to the fluent material. The stimulation apparatus may thus be configured to apply electromagnetic radiation to the fluent material in addition to applying an electric field to the fluent material. As mentioned above, a stimulus comprising visible light may be appropriate for certain forms of particle. The particles may respond to the electromagnetic radiation of themselves. Alternatively the fluent material may comprise a compound, such as a label, which is operative to cause the particles to respond to electromagnetic radiation. More specifically the fluent material may comprise a fluorochrome which is operative to re-emit light upon light excitation. The stimulation apparatus may comprise a source of electromagnetic radiation, e.g. a source of light, such as a light emitting diode or a laser diode. A source of electromagnetic radiation and supporting apparatus, such as focussing optics, may be incompatible with a semiconductor fabrication process, such as CMOS. The source of electromagnetic radiation may therefore be constituted apart from the integrated circuit comprising the particle sensing apparatus.

According to a second aspect of the present invention there is provided biological analysis apparatus comprising biological sensing apparatus according to the first aspect of the present invention. The biological analysis apparatus may be configured to be operable as a flow cytometer. The biological analysis apparatus may further comprise control apparatus. The control apparatus may be configured to control the particle sensing apparatus. For example the control apparatus may be configured to control the sensing arrangement with regards to when a particle is sensed. By way of further example and where the biological sensing apparatus comprises stimulation apparatus the control apparatus may be configured to determine if electrodes comprised in the particle sensing apparatus and the stimulation apparatus are used for actuation, stimulation or sensing. By way of yet further example and where the biological sensing apparatus comprises an array of electrodes the control apparatus may be configured to determine a sequence of operation of electrodes in the array. The control apparatus may be constituted by any suitable electronic arrangement, such as a microprocessor or a configurable electronic circuit, such as a Field Programmable Gate Array (FPGA).

The biological analysis apparatus may comprise flow inducing apparatus, i.e. a pump, which is operative to induce a flow of fluent material through the flow arrangement. The flow inducing apparatus may be controlled, for example in respect of a rate of flow of fluent material through the flow arrangement, in dependence on an output from the particle sensing apparatus. The control apparatus may be operative to receive an output from the particle sensing apparatus and to provide an output to the flow inducing apparatus in dependence thereon. The particle sensing apparatus as described elsewhere herein may be operative to provide for determination of a rate of flow of fluent material through the flow arrangement, the rate of flow being received by the control apparatus. Where the particle sensing apparatus comprises plural spaced apart sensing arrangements with each sensing arrangement being operative to sense particles, the rate of flow may be determined in dependence on the separation between the sensing arrangements being known and a time between sensing of a particle by different sensing arrangements. Alternatively or in addition characterisation of at least one particle as described elsewhere herein may be compared with a predetermined criterion and the flow inducing apparatus may be controlled in dependence on the comparison. For example characterisation of the at least one particle may comprise a level of confidence value which is compared with a predefined value. More specifically if the level of confidence value is below the predefined value the flow inducing apparatus may be operative to reduce a rate of flow of the fluent material to thereby provide for improved characterisation.

Alternatively or in addition the biological analysis apparatus may further comprise processing apparatus. The processing apparatus may be configured to receive signals from the particle sensing apparatus and to convert the received signals to digital form. The processing apparatus may therefore comprise an analogue-to-digital converter and whatever signal conditioning circuitry may be required, such as an amplifier and an anti-aliasing filter. The processing apparatus may be constituted by any suitable electronic arrangement, such as a separate analogue-to-digital converter circuit, a separate amplifier circuit and a separate filter circuit or a configurable integrated circuit, such as an FPGA, or a dedicated integrated circuit, such as an Application Specific Integrated Circuit (ASIC), comprising such circuits.

Alternatively or in addition the biological analysis apparatus may further comprise an analysis arrangement. The analysis arrangement may be configured to make determinations with regards to particles comprised in the fluent material in dependence on at least one output from the particle sensing apparatus. For example the analysis arrangement may be operative to make determinations in dependence on electric field measurements made by the particle sensing apparatus after analogue to digital conversion. Determinations may be made in respect of the like of the density of particles comprised in the fluent material, differentiation of one form of particle from another and characteristics of particles, such as in respect of dimensions or composition. The analysis arrangement may be constituted by any suitable electronic arrangement, e.g. a general purpose computer, such as a Personal Computer (PC), an embedded microprocessor, a configurable electronic circuit, such as a FPGA or the like. Further embodiments of the second aspect of the present invention may comprise one or more further features of the first aspect of the present invention.

According to a third aspect of the present invention there is provided a biological sensing method for sensing particles comprised in fluent material, the method comprising:
containing fluent material in a flow arrangement and providing for flow of the fluent material therethrough;
sensing an electrical property of particles comprised in the fluent material as the fluent material flows through the flow arrangement, the electrical property of the particles being sensed by particle sensing apparatus disposed relative to the flow arrangement, the particle sensing apparatus being comprised in an integrated circuit formed by a semiconductor fabrication process.

Embodiments of the third aspect of the present invention may comprise one or more features of any previous aspect of the present invention.

According to a further aspect of the present invention there is provided a sensing arrangement configured to sense particles comprised in fluent material, the sensing arrangement comprising: particle sensing apparatus comprised in an integrated circuit formed by a semiconductor fabrication process; and a flow arrangement configured to contain and provide for flow of fluent material, the particle sensing apparatus being disposed relative to the flow arrangement such that the particle sensing apparatus is operative to sense particles comprised in the fluent material as the fluent material flows through the flow arrangement. The fluent material may comprise at least one of a liquid and a gas. Alternatively or in addition the particles may be entrained in a fluid carrier. Alternatively or in addition the particles may be dispersed through a fluid carrier. Further embodiments of the further aspect of the present invention may comprise one or more features of any previous aspect of the present invention.

According to a yet further aspect of the present invention there is provided a sensing arrangement configured to sense fluent material, the sensing arrangement comprising: sensing apparatus comprised in an integrated circuit formed by a semiconductor fabrication process; and a flow arrangement configured to contain and provide for flow of fluent material, the sensing apparatus being disposed relative to the flow arrangement such that the sensing apparatus is operative to sense the fluent material as the fluent material flows through the flow arrangement. The fluent material may comprise particles. The sensing apparatus may be particle sensing apparatus configured to sense particles comprised in the fluent material. Further embodiments of the yet further aspect of the present invention may comprise one or more features of any previous aspect of the present invention.

BRIEF DESCRIPTION OF DRAWINGS

Further features and advantages of the present invention will become apparent from the following specific description, which is given by way of example only and with reference to the accompanying drawings, in which:

FIG. 1 is a block diagram representation of biological analysis apparatus according to the present invention;

FIG. 2 is a block diagram representation of the biological sensing apparatus comprised in the biological analysis apparatus of FIG. 1;

DESCRIPTION OF EMBODIMENTS

Figure 3:
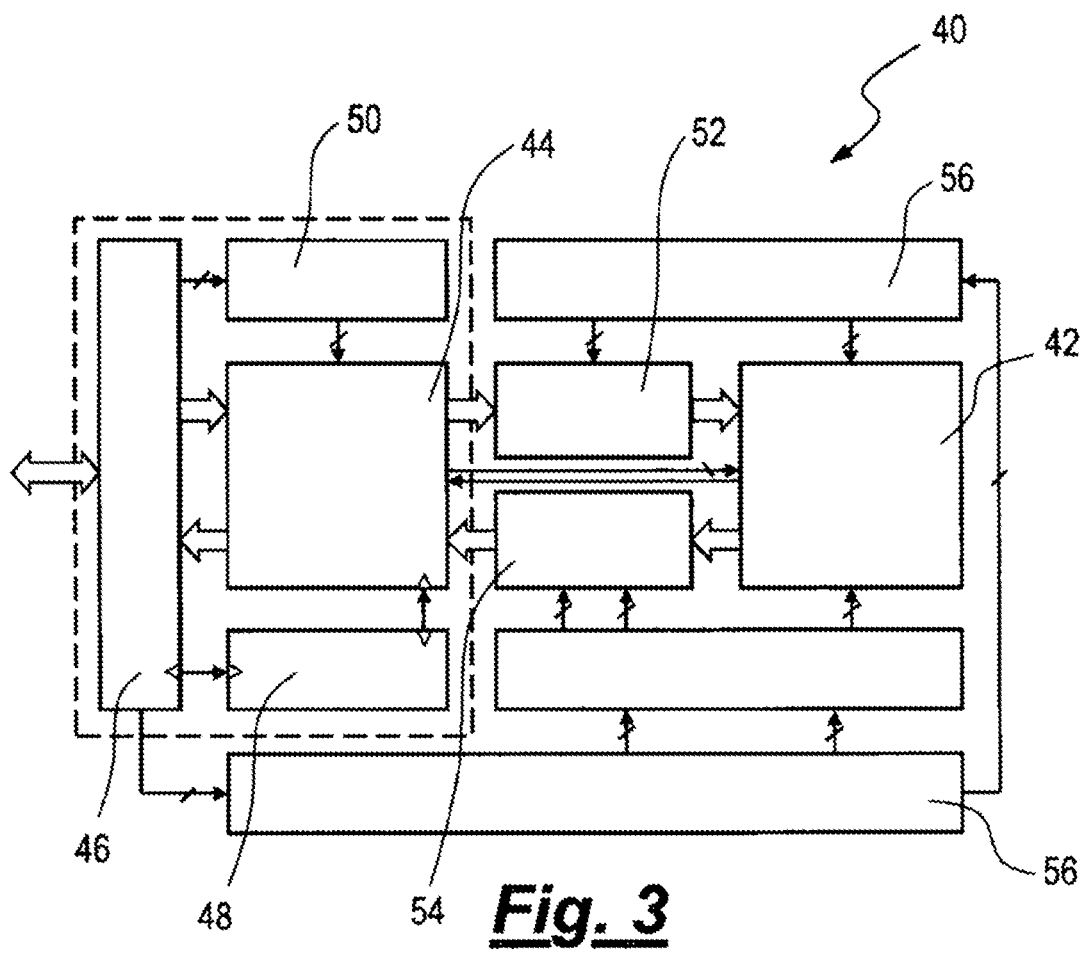
FIG. 3 is a block diagram representation of a particular embodiment of biological analysis apparatus.

A block diagram representation of biological analysis apparatus 10 according to the present invention is shown in FIG. 1. The biological analysis apparatus 10 comprises biological sensing apparatus 12, control and processing apparatus 14 (which constitutes a control apparatus) and an analysis arrangement 16. The biological sensing apparatus 12 receives a flow of analyte in the form of phosphate buffered saline (PBS) 18 (which constitutes fluent material) in which biological cells (which constitute biological particles) are suspended. An alternative to PBS may be used on account of the present approach providing for sensing which is independent of the suspension material. The flow of analyte is directed through the biological sensing apparatus 12 where it is subject to actuation, stimulation and sensing, as described in detail below, before exiting 20 from the biological sensing apparatus 12. The control and processing apparatus 14 controls the operation of electronic circuitry comprised in the biological sensing apparatus 12, e.g. in respect of determining a sequence of operation of the electronic circuitry and the application of stimulation signals to the analyte, and also processes signals sensed by the biological sensing apparatus 12. Processing comprises the like of amplification of sensed signals, analogue to digital conversion of sensed signals and storage of converted sensed signals. As shown in FIG. 1 the biological analysis apparatus 10 further comprises a pump (which constitutes a flow inducing apparatus 90 schematically shown in FIGS. 1 and 2) which is operative to push or draw analyte through the biological sensing apparatus 12.

The analysis arrangement 16 is operative to make at least one analytical determination in dependence on the stored converted sensed signals. Analytical determinations comprise: detecting the presence of biological cells in the analyte; counting biological cells in the analyte; differentiating one form of biological cell from another; and determining a characteristic of biological cells in the analyte, such as a cell dimension or a cell composition. The analysis arrangement 16 is also operative to provide for supervisory control of the control and processing apparatus 14, e.g. in respect of a change in the form of control of the biological sensing apparatus 12 exercised by the control and processing apparatus 14. The control and processing apparatus 14 is constituted by any suitable electronic arrangement, such as a separate analogue-to-digital converter circuit, a separate amplifier circuit and a separate electronic memory circuit, or a configurable integrated circuit, such as an FPGA, comprising the digital circuits and an ASIC comprising the analogue circuits. The analysis arrangement 16 is constituted by any suitable electronic arrangement, e.g. a general purpose computer, such as a PC, an embedded microprocessor, a configurable electronic circuit, such as an FPGA or the like. The control and processing apparatus 14 and analysis arrangement 16 are constituted apart from each other, e.g. as separate modules, or constituted together, e.g. in a same integrated circuit or same general purpose computer.

FIG. 3, which is described further below, represents a particular embodiment in which components of the biological analysis apparatus are constituted separately in a CMOS ASIC, an FPGA, and a PC, amongst other things. The embodiment of FIG. 3 is appropriate as a prototype and provides for configurability for the like of system development or evaluation. A form of the biological analysis apparatus which is suitable for manufacture is constituted differently by constituting components within the same integrated circuit or module. For example and as mentioned above the functionality of the analysis arrangement 16 is incorporated in the FPGA and the functionality of the control and processing apparatus 14 is incorporated in the CMOS ASIC. Modifying the embodiment of FIG. 3 in this fashion is within the ordinary design capabilities of the person skilled in the art.

Figure 4:
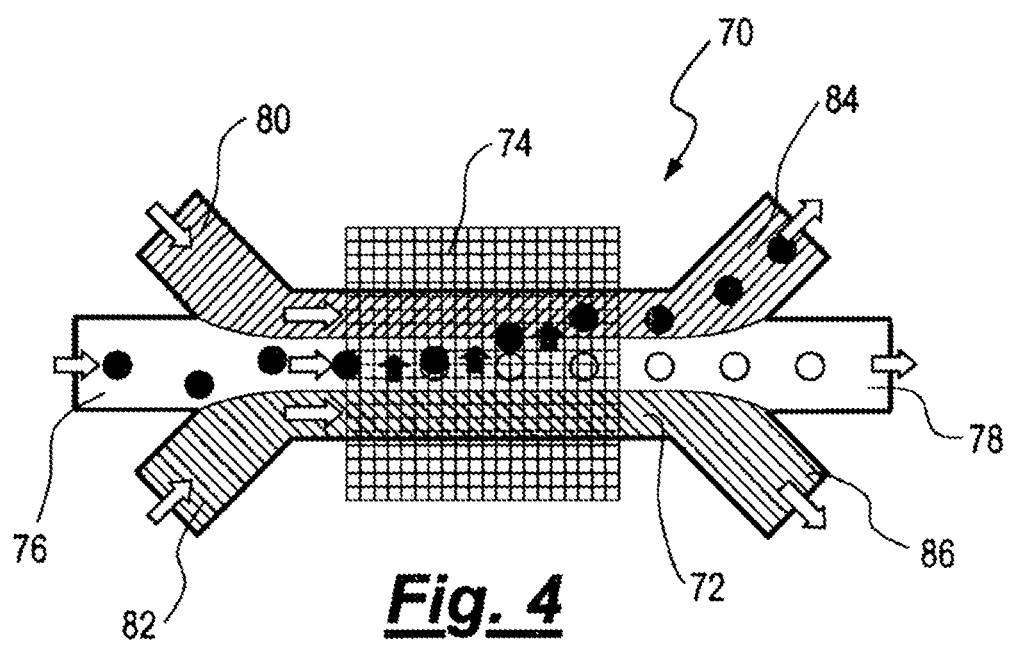
FIG. 4 is a representation of a flow arrangement comprised in the biological sensing apparatus of FIG. 2.

A block diagram representation of the biological sensing apparatus 12 comprised in the biological analysis apparatus of FIG. 1 is shown in FIG. 2. The biological sensing apparatus 12 comprises a flow arrangement 30, which receives the analyte 18 and provides for flow of the analyte before the analyte exits 20 from the flow arrangement. The flow arrangement 30 is described further below with reference to FIG. 4. The biological sensing apparatus 12 also comprises a two-dimensional array of electrodes 32. Although FIG. 2 shows the flow arrangement 30 and the array of electrodes 32 side-by-side, the flow arrangement 30 and the array of electrodes 32 are disposed in relation to each other such that the array of electrodes 32 is above a main channel of the flow arrangement 30; this disposition is shown in FIG. 4. The biological sensing apparatus 12 further comprises a sensing circuit 34 and an electric field source circuit 35, which are each electrically coupled to the array of electrodes 32. The array of electrodes 32, the sensing circuit 34 and the electric field source circuit 35 are comprised in a particle sensing apparatus and particle stimulation apparatus 31 (schematically represented by dotted line block in FIG. 2), which is comprised in the biological sensing apparatus 12, as shown in FIG. 2. (As further discussed below in connection with the embodiment 40 of FIG. 3 in more detail, the array of electrodes 32, the sensing circuit 34 and the electric field source circuit 35 are all comprised in a CMOS ASIC 42.)

The sensing circuit 34 is operative to provide for biological cell sensing by way of the array of electrodes 32 and the electric field source circuit 35 is operative to provide for biological cell stimulation and actuation by way of the array of electrodes 32 as is described in detail below. The array of electrodes 32 therefore comprises pairs of sensing electrodes and pairs of stimulation electrodes. The array of electrodes 32, the sensing circuit 34 and the electric field source circuit 35 are constituted by a CMOS process such as a 0.35 micron CMOS process.

Considering the embodiment 40 of FIG. 3 in more detail, the array of electrodes 32, the sensing circuit 34 and the electric field source circuit 35 are all comprised in a CMOS ASIC 42. Each electrode in the array 32 is 18 microns by 18 microns with a 2 micron gap between electrodes whereby the array pitch is 20 microns. The thickness and permittivity of the standard polyimide top layer of the ASIC provides insufficient capacitance for proper engagement of the electrodes 32 with the analyte. According to a first approach the polyimide top layer is removed by oxygen plasma ashing to reveal the silicon nitride layer underneath or the fabrication process lacks the polyimide layer deposition step so no removal is required. The hydrophilic nature of the silicon nitride layer provides for maximum exposure of the analyte surface area to the electrodes 32. According to a second approach the polyimide top layer is removed as per the first approach or no polyimide layer is deposited and a layer of polyvinylidene fluoride (PVDF) is provided over the exposed silicon nitride layer. The PVDF layer is provided by spin coating onto the exposed silicon nitride layer. Alternatively PVDF is formed separately as a membrane which is placed over the ASIC to thereby cover the exposed silicon nitride layer. After the removal of the polyimide top layer or the provision of a PVDF layer the ASIC 42 is disposed, as is mentioned above, relative to the flow arrangement 30 of FIG. 2 such that the array of electrodes 32 engages with the analyte flowing through the flow arrangement 30. The sensing circuit 34 and the electric field source circuit 35 of the ASIC comprise binary to decimal decoders and memory for row and column addressing of the array of electrodes 32, global configuration logic and bias circuitry for the sensor output signal paths. The global configuration logic is operative to provide for the like of memory resetting and the gating of control signals with respect to a global reset signal to ensure all control lines power up in a known state. The embodiment of FIG. 3 further comprises a Printed Circuit Board (PCB) which supports and provides for electrical connectivity for electrical circuits which support the ASIC 42. The electrical circuits comprised in the PCB includes an FPGA 44 which is configured to provide various digital functions including the generation of stimulus and actuation signals, addressing of individual electrodes in the array of electrodes 32 and communication with a Universal Serial Bus (USB) module 46. The FPGA 44 is a Xilinx Spartan-3. The FPGA 44 is operative to generate a stimulation signal in the form of an m-sequence by way of a linear feedback shift register or otherwise as would be within the ordinary design skills of the person skilled in the art. Alternatively an m-sequence is provided by an external signal generator which provides for ease of change of m-sequence characteristics.

The PCB further includes a Phase Locked Loop (PLL) module 48, which is operative to provide integrated clock synthesis for the FPGA, and a switching power supply 50 for the FPGA. The PLL module 48 is operative to generate stable and phase-synchronous clocks from a crystal oscillator for use in the FPGA in dependence on operation of clock management circuits comprised in the FPGA which are operative to derive subsidiary clock signals from a main clock received from the PLL module. The switching power supply 50 comprises switched-mode power supply units which are operative to generate 3.3V and 1.8V from a 5V USB bus voltage received by the apparatus. The PCB also includes input signal conditioning circuitry 52 which is configured to receive stimulus and actuation signals from either the FPGA or from the external (un-illustrated) signal generator, generate differential stimulus signals from single ended stimulus signals and provide for programmable gain amplification of the voltage swing of the stimulus and actuation signals. In addition the PCB includes output signal conditioning circuitry 54 which performs a variety of functions including fixed gain, low distortion amplification of sensed single ended and differential signals followed by programmable gain amplification or attenuation of such initially amplified signals under the control of a PC. The output signal conditioning circuitry 54 also includes a 250 M sample per second (MSPS) analogue-to-digital converter, which is operative to receive amplified sensed signals and provide a converted bit stream to the FPGA 44 along with a data output clock which is synchronous with the bit stream. The data output clock is fed forwards to the FPGA 44 as a reference for clock management circuitry comprised in the FPGA. Use of the data output clock as a reference by the clock management circuitry provides for removal of trip latency from the converted bit stream to thereby remove time delay caused by the sensing circuitry. The PCB also comprises support circuitry such as power supply and regulation circuitry 56.

As described above the PCB comprises a USB module 46. The USB module provides for communication with a PC running Python/Numpy software which is operative to perform the functions of the analysis arrangement 16 of FIG. 1. More specifically the PC is operative to configure the ASIC 42 and the circuits comprised in the PCB. In addition the PC receives real time sensed data or blocks of data which have been acquired and stored locally from the FPGA 44. More specifically the PC is operative to decode the received m-sequence encoded data by application of a Hadamard transform, such as the Fast Hadamard transform, to thereby provide for rapid calculation of the impulse response. The fast Hadamard transform is given by:

$$\Psi' = \frac{1}{2^{m-1}} \xi_1 H \xi_2 \eta$$

where $\Psi'$ is the estimated output spectrum of the system under test, m is the sequence order, H is the Hadamard matrix, $\eta$ is the measured m-sequence encoded response, and $\xi_1$ and $\xi_2$ are the encode and decode matrices for transforming m-sequence data into the correct order for use with the Hadamard matrix. In one form, $\xi_1$ and $\xi_2$ are equal to each other. The PC is further operative to perform a Fast Fourier Transform (FFT) on the decoded data to thereby provide frequency domain data. The frequency domain data is then displayed for user interpretation. The frequency domain data provides for characterisation of the biological cells in the analyte, such as in respect of their dimensions and composition whereby the nature of a particular cell type can be determined or different cell types can be differentiated. The PC is also operative to count biological cells present in the analyte and to determine a density of cells present in the analyte in dependence on the flow rate and volume of the flow arrangement with the count and density information being displayed to the user.

A representation of a flow arrangement 30, 70 comprised in the biological sensing apparatus of FIG. 2 is shown in detail in FIG. 4. The flow arrangement 70 of FIG. 4 is formed from PMMA or silicone and has a length of about 25 mm and a width of about 10 mm. The flow arrangement 70 comprises a main channel 72 through which the analyte flows. The array of electrodes 74, which comprises pairs of sensing electrodes and pairs of stimulation electrodes, is disposed above the main channel 72 so that the electrodes engage with the analyte as the analyte flows through the main channel. As is described above the array of electrodes 74 is comprised in a CMOS ASIC. The CMOS ASIC and the flow arrangement 70 are releasably attached to each other by way of a fastener arrangement comprising a silicone gasket layer such that a proper relative disposition of electrodes and main channel is achieved. The flow arrangement also comprises a sample inlet 76 which receives the analyte, e.g. by way of injection, and a sample outlet 78 at an opposite end of the flow arrangement from the sample inlet 76. The sample inlet 76 and the sample outlet 78 are each in fluid communication with the main channel 72. In addition the flow arrangement comprises first and second further inlets 80, 82. The first further inlet 80 is disposed laterally on one side of the sample inlet 76 and the second further inlet 82 is disposed laterally on the other opposite side of the sample inlet. Each of the first and second further inlets 80, 82 are in fluid communication with the main channel 72. The flow arrangement yet further comprises first and second further outlets 84, 86 disposed at opposite sides of the opposite end of the flow arrangement to the first and second further inlets 80, 82, with the first and second further outlets 84, 86 being in fluid communication with the main channel 72. In use a sheath fluid, such as phosphate buffered saline (PBS), is received by each of the first and second further inlets 80, 82 to thereby provide for a flow of sheath fluid in the main channel, the flow of sheath fluid being lateral of a flow of analyte received by the sample inlet 76. The flow of sheath fluid provides for registration of the biological cell comprising analyte with the array of electrodes 74 and also helps preserve the integrity of the flow of analyte as it progresses though the main channel. The array of electrodes 74 can be used to actuate biological cells comprised in the analyte by selective addressing of electrodes within the array and application of an actuating signal to the selectively addressed electrodes. Electrode addressing and application of the actuating signal is by way of the electronic circuitry described above. More specifically a first sinusoidal signal or a digital clock is applied to a first central row of electrodes in the array 74 (where an electrode row is in the same direction as analyte flow) and second and further sinusoidal signals or clocks are applied to each of second and further rows of electrodes in the array 74 to one side of the first central row of electrodes. The sinusoidal signals or clocks as applied to the first, second and further rows of electrodes have at least one of different phase and amplitude whereby a force is applied to biological cells in the analyte such that the biological cells are moved in a direction perpendicular to the direction of flow of analyte as shown in FIG. 4. FIG. 4 shows cells being steered such that they leave the flow arrangement 70 by way of the first further outlet 84. Different forms of actuation can be provided for by way of different electrode addressing patterns and the application of different actuating signals. Such different forms of actuation include, for example, moving a cell or a group of cells to a desired part of the array, such as a part of the array having electrodes of a size corresponding to the size of cell to provide for dimension appropriate stimulation and sensing, where the array of electrodes comprises electrodes of different sizes. By way of further example another form of actuation involves moving different cells to different parts of the array before sensing takes place so that sensing may be carried out on plural cells at the same time by the different parts of the array. It is to be noted that each electrode of the array can be selectively used for actuation, stimulation and sensing. Stimulation and sensing are described further below. Fluid flow through the flow arrangement 30, 70 can be reversed with stimulation, sensing and actuation of particles comprised in the fluid being operative as described elsewhere herein.

Stimulation and sensing comprises electric field stimulation and electric field sensing. A biological cell cooperates with such an applied electric field whereby the electric field is disturbed. Different sizes of a particular type of biological cell will disturb an applied electric field in a different fashion. Also different types of biological cell will disturb an applied electric field in a different fashion. Sensing of the electric field in dependence on the disturbance can therefore provide for the like of detection of the presence of biological cells, determination of relative sizes of cells and differentiation of different types of cell from each or one another. In certain arrangements of the present form, the analyte comprises an electrically sensitive label to provide an enhanced response or capability. Examples of electrically sensitive label include: latex microbeads having specific antibody coatings for use in a basic electrical HIV test; microbeads of either different materials, such as polystyrene or rubber, or of different sizes and having different antibody coatings which provide for identification of biological cell types; and conductive particles, such as iron microbeads, which are operative to absorb the electric field. Electric field stimulation and electric field sensing can both be accomplished within a CMOS ASIC of the form described above. More specifically the array of electrodes 32, 74 is used for both electric field stimulation and electric field sensing, with different sets of electrodes being used for stimulation and sensing at any one time, although it should be noted that each electrode can be used for stimulation and sensing at different times.

The pump (which constitutes the flow inducing apparatus 90) of the biological analysis apparatus 10 of FIG. 1 is controlled in dependence on at least one of: a rate of flow of analyte through the biological sensing apparatus 12; and a level of confidence of characterisation of the analyte flowing through the biological sensing apparatus 12. Considering rate of flow of analyte further, the separation between pairs of electrodes of the biological sensing apparatus 12 is known and the time of travel of biological cells between pairs of electrodes is determined by the control and processing apparatus 14 (which constitutes the control apparatus). The control and processing apparatus 14 is then operative to determine the speed of movement of biological cells through the biological sensing apparatus 12. The control and processing apparatus 14 (which constitutes the control apparatus) is then operative to control the pump in dependence on the determined speed. For example, if the determined speed is below a predetermined value the control and processing apparatus 14 is operative to increase the flow rate by controlling the pump. Considering level of confidence of characterisation of the analyte further, the control and processing apparatus 14 (which is operatively coupled to the analysis arrangement 16 as shown in FIG. 2), is operative to characterise biological cells and to determine a level of confidence of the characterisation. The control and processing apparatus 14 (which is operatively coupled to the analysis arrangement 16) is further operative to compare the determined level of confidence with a predetermined level and then to control the pump in dependence thereon. If the determined level of confidence is below the predetermined level, the control and processing apparatus 14 is operative to reduce the rate of flow by controlling the pump to thereby provide for improved characterisation of the biological cells.

Figure 5:
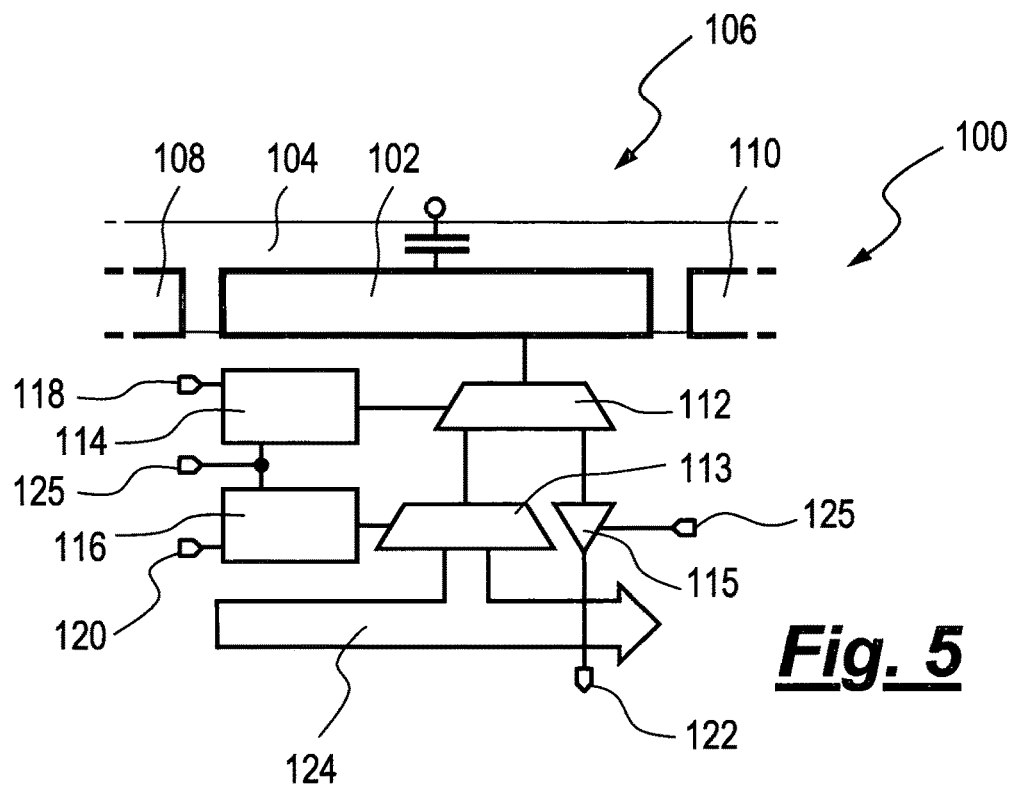
FIG. 5 is a circuit representation of a single ended sensing and stimulation cell.

A sensing and stimulation cell 100 configured for single ended operation is shown in FIG. 5. The sensing and stimulation cell 100 of FIG. 5 (which may be comprised in the particle sensing apparatus and particle stimulation apparatus 31) comprises a single electrode 102, which is comprised in the array of electrodes 32, 74. A dielectric layer 104 is present between the electrode 102 and the analyte 106. The dielectric layer 104 also provides for isolation between the electrode 102 and neighbouring electrodes. FIG. 5 shows second and third electrodes 108, 110 of neighbouring sensing and stimulation cells. The sensing and stimulation cell 100 further comprises multiplexer circuitry comprising a first multiplexer 112 and a second multiplexer 113 which provide for one of four states selected in accordance with first and second state selection bits 118, 120. The sensing and stimulation cell 100 also comprises an output buffer 115 which is enabled by a select bit 125. The sensing and stimulation cell 100 also comprises a first memory bit 114 and a second memory bit 116. The first memory bit 114 stores the state of the first state selection bit 118 and the second memory bit 116 stores the state of the second state selection bit 120. Each of the first and second memory bits 114, 116 provides for persistence of application to the first and second multiplexers 112, 113 of their respective state selection bits. Persistence of application of the state selection bits is required because the addressing period of each electrode in the array is shorter than the time required for application of the stimulation signal to the electrode and the time required to acquire a signal from the electrode. The addressing period for each electrode is short in view of the large number of electrodes in the array. The first and second memory bits 114, 116 are constituted in Static Random Access Memory (SRAM).

As mentioned above the first and second multiplexers 112, 113 of FIG. 5 provide for one of four states and the address-sensitive selection bit 125 is asserted to pass the first and second state selection bits 118, 120 to the respective first and second memory bits 114, 116. To provide for one of the four states, the electrode is addressed with the address-sensitive selection bit 125 and then the first and second state selection bits 118, 120 are stored as the first and second memory bits 114, 116. The configuration of the first and second memory bits 114, 116 provides for one of the four states. In a first state and when both the first and second state selection bits 118, 120 are at zero the electrode 102 is connected by way of a switch to common ground potential.

In a second state and when the first state selection bit 118 is at zero and the second state selection bit 120 is at one to enable the output buffer 115 and configure the electrode 102 for sensing whereby the electrode is connected to a sensor output pin 122 via the addressable output buffer 115.

The sensor output pin 122 is electrically connected to the part of the sensing circuit 34 which is operative to process sensed signals, as described above. In a third state and when the first state selection bit 118 is at one and the second state selection bit 120 is at zero the electrode 102 is configured for stimulation whereby the electrode receives a stimulation input from a signal bus 124. The signal bus 124 is electrically connected to the part of the electric field source circuit 35 which is operative to generate stimulation signals, as described above. In a fourth state and when the first state selection bit 118 is at one and the second state selection bit 120 is at one the electrode 102 is configured for actuation whereby the electrode receives an actuation input from the signal bus 124. The signal bus 124 is electrically connected to the part of the electric field source circuit 35 which is operative to generate actuation signals, as described above. The signal bus 124 thus carries both a stimulation input and an actuation input with the second state selection bit 120 being operative to select one of these two inputs depending on its state. Each electrode in the array of electrodes comprises the multiplexer and memory circuitry shown in FIG. 5. It can thus be appreciated that the sensing and stimulation cell 100 of FIG. 5 and indeed each of every sensing and stimulation cell in the ASIC can be used for one of actuation, stimulation and sensing. Considering stimulation further, a stimulation signal is applied between one electrode and the next but one electrode. In FIG. 5 the stimulation signal is, for example, be applied between the second and third electrodes 108, 110. Turning now to sensing and where the stimulation signal is applied between the second and third electrodes 108, 110, the first electrode 102 is configured for sensing. The pattern of stimulation and actuation can be changed from that described above and indeed from cycle to cycle. The pattern of stimulation and actuation is determined by the control and processing apparatus 14 with the control and processing apparatus 14 being programmed to provide for different desired patterns. For example and according to one approach, the electrodes in the array are subject to stimulation such that the row of electrodes above and the row of electrodes below a row of electrodes containing an electrode that is addressed for sensing are stimulated to thereby reduce coupling of the stimulus signal directly across the electrode being sensed.

Figure 6:
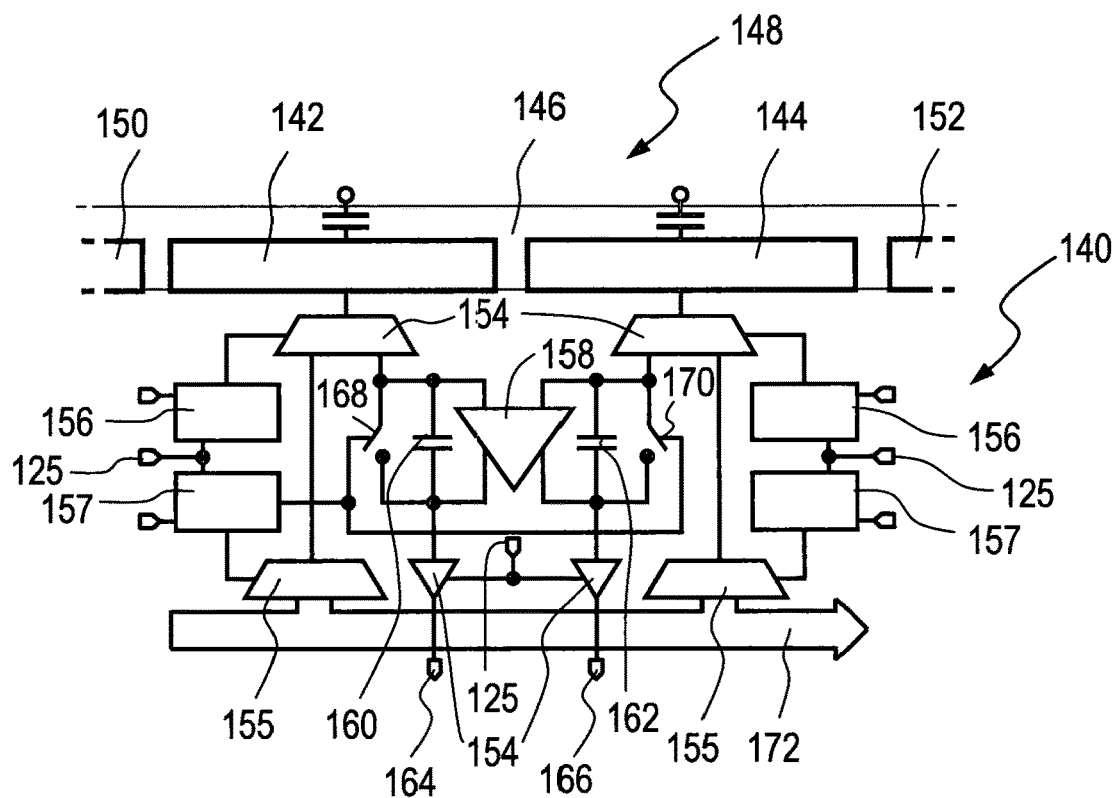
FIG. 6 is a circuit representation of a differential sensing and stimulation cell.

A sensing and stimulation cell 140 configured for differential operation is shown in FIG. 6. The sensing and stimulation cell 140 of FIG. 6 (which may be comprised in the particle sensing apparatus and particle stimulation apparatus 31) comprises first and second adjacent electrodes 142, 144. As with the sensing and stimulation cell 100 of FIG. 5 a dielectric layer 146 is present between the first and second electrodes 142, 144 and the analyte 148. The dielectric layer 146 also provides for isolation between the first and second electrodes 142, 144 and neighbouring electrodes. FIG. 6 shows third and fourth electrodes 150, 152 of neighbouring sensing and stimulation cells. In common with the sensing and stimulation cell 100 of FIG. 5 each of the first and second adjacent electrodes 142, 144 has a first multiplexer 154 and a second multiplexer 155 and state selection bits of first and second memory bits 156, 157 associated with them to provide for selection of one of the four states described above with reference to FIG. 5.

The sensing and stimulation cell 140 of FIG. 6 further comprises a fully-differential amplifier 158, a first capacitor 160 and a second capacitor 162. The fully-differential amplifier 158 receives a connection from the first electrode 142 at one of its inputs and receives a connection from the second electrode 144 at its other input. One of the two outputs from the differential amplifier 158 is electrically connected to a first sensor output pin 164 and the other output from the differential amplifier 158 is electrically connected to a second sensor output pin 166 through respective address-sensitive output buffers 154. The first capacitor 160 is connected between an input and an output of the differential amplifier 158 and the second capacitor 162 is connected between the other input and the other output of the differential amplifier 158. A first switch 168 is connected across the first capacitor 160 and a second switch 170 is connected across the second capacitor 162. Both of the first and second switches are under the control of the second memory bit 157 associated with the first electrode 142 such that upon selection of the sense state the first and second switches are open whereby the fully-differential amplifier 158 is operative to pass a differential signal sensed between the first and second electrodes 142, 144 to the first and second sensor output pins 164, 166. Differential sensing is accomplished by way of two adjacent electrodes as thus described with reference to FIG. 6. When the first memory bit 156 is zero and the second memory bit 157 is one, the first and second capacitor switches 168 and 170 are closed to thereby short-circuit the first and second capacitors. Short-circuiting of the first and second capacitors equalises the charge across their respective plates to thereby eliminate any difference in apparent voltage across them.

Stimulation in FIG. 6 is accomplished as described above with reference to FIG. 5 by way of the third and fourth electrodes 150, 152 on each side of the two adjacent electrodes 142, 144 except as described herein below. Actuation is accomplished by making the appropriate state selections in respect of the first to fourth electrodes 142, 144, 150, 152 as described above with reference to FIG. 5 except as will now be described. The signal bus 172 of the circuit of FIG. 6 is limited to carrying only two signals. The circuit of FIG. 6 therefore comprises a further un-illustrated multiplexer which is operative to select either two complementary, i.e. out of phase, stimulation signals or two complementary, i.e. out of phase, actuation signals. The circuit of FIG. 6 is operative such that each pair of complementary signals, i.e. stimulus or actuation, is applied simultaneously at any one time. The circuit of FIG. 6 is operated optionally such that it is subject to stimulation in a single ended fashion.

A form of stimulation and sensing employed in addition to electric field stimulation and electric field sensing comprises optical stimulation and electro-optic sensing. According to this form optical stimulation is provided by radiating the flow arrangement with visible light from a light source, such as a laser diode or an LED. In accordance with normal procedure for optical stimulation the analyte comprises an appropriate fluorochrome in certain arrangements of the second form to thereby provide for sensing of light absorbed and emitted on account of the fluorochrome in addition to transmitted and scattered light. Sensing is accomplished by an array of photosensitive junctions comprised in the ASIC, such as an array of photodiodes (PDs). The present form is combined with the previous form such that optical and electric field sensing are combined. More specifically the photosensitive junctions are distributed amongst the array of electrodes. Selection of photosensitive junctions is by way of an addressing and sensed signal readout scheme of the same form as described above with reference to FIGS. 5 and 6.

The invention claimed is:

1. A biological analysis apparatus, comprising:
a fluent material comprising biological particles;
a flow arrangement comprising a channel through which the fluent material flows;
a biological sensing apparatus, comprising plural sensing and stimulation cells all comprised in a same integrated circuit formed by a semiconductor fabrication process, wherein the integrated circuit is disposed relative to the channel, wherein each of the plural sensing and stimulation cells comprises an electric field applying apparatus and an electric field sensing apparatus, wherein the electric field applying apparatus comprises an electric field source circuit and a pair of electric field applying electrodes, the pair of electric field applying electrodes being electrically coupled to the electric field source circuit, the pair of electric field applying electrodes being disposed on a first side of the channel, and each of the pair of electric field applying electrodes has a dielectric layer which electrically isolates the electric field applying electrode from fluent material in the channel, wherein the electric field sensing apparatus comprises a sensing circuit and a pair of sensing electrodes, the sensing circuit being electrically coupled to the pair of sensing electrodes, the pair of sensing electrodes being disposed on the first side of the channel, and each of the pair of sensing electrodes has a dielectric layer which electrically isolates the sensing electrode from fluent material in the channel, wherein in each of the plural sensing and stimulation cells the pair of electric field applying electrodes has a first electrode and the pair of sensing electrodes has a second electrode, the first and second electrodes being structurally separate electrodes;
a flow inducing apparatus causing the fluent material to flow through the channel; and
a control apparatus electrically coupled to the flow inducing apparatus, and to the electric field source circuit and the sensing circuit of each of the plural sensing and stimulation cells, the control apparatus comprising an electronic circuit having a circuit structure and/or a non-transitory memory having programmed instructions, to control the flow inducing apparatus to cause the fluent material containing the biological particles to flow through the channel, control each of the electric field source circuits to apply an electric field to a respective one of the biological particles comprised in the fluent material by way of the pair of electric field applying electrodes as the fluent material flows through the channel, and control each of the sensing circuits to sense respective sensed electric field, wherein the biological particle cooperates with the applied electric field whereby the applied electric field is disturbed and the biological particle can be characterized, and wherein the sensing circuit senses by way of the pair of sensing electrodes the sensed electric field corresponding to the applied electric field as disturbed by the biological particle so as to characterize the biological particle, wherein the electric field applied by the electric field source circuit of each of the plural sensing and stimulation cells is a pseudo-random noise signal, wherein the pseudo-random noise signal is an m-sequence, wherein the control apparatus compares each applied electric field with the respective sensed electric field corresponding to the applied electric field as disturbed by the respective biological particle to characterize the biological particle, wherein comparing each applied electric field with the respective sensed electric field comprises at least one of: cross-correlation of the applied electric field and the respective sensed electric field; and determining a transfer function based on the applied electric field and the respective sensed electric field.

2. The biological analysis apparatus according to claim 1, wherein the fluent material comprises at least one electrically sensitive label.

3. The biological analysis according to claim 1, wherein the pair of electric field applying electrodes and the pair of sensing electrodes in each of the plural sensing and stimulation cells are disposed side by side.

4. The biological analysis apparatus according to claim 1, wherein at least one of an electric field applying electrode and a sensing electrode of each of the plural sensing and stimulation cells has a dimension of less than one of 100 microns, 50 microns, 30 microns, 20 microns, 15 microns, 10 microns, 5 microns, 3 microns and 1 micron.

5. The biological analysis apparatus according to claim 1, wherein the plural sensing and stimulation cells form an array of pairs of sensing electrodes, the array of pairs of sensing electrodes extending in a direction of flow of the fluent material through the channel and extending in a direction orthogonal to the direction of the flow of the fluent material.

6. The biological analysis apparatus according to claim 1, wherein the sensing circuit of each of the plural sensing and stimulation cells is controlled by the control apparatus to sense an electrodynamic field.

7. The biological analysis apparatus according to claim 1, wherein the electric field source circuit of each of the plural sensing and stimulation cells is controlled by the control apparatus to apply an electrodynamic field to the fluent material.

8. The biological analysis apparatus according to claim 1, wherein the semiconductor fabrication process is a metal-oxide semiconductor process.

9. The biological analysis apparatus according to claim 1, wherein the electric field source circuit of each of the plural sensing and stimulation cells is controlled by the control apparatus to apply a varying electric field.

10. The biological analysis apparatus according to claim 1, wherein the electronic circuit comprised in the control apparatus comprises at least one of a microprocessor, a configurable electronic circuit and an application specific integrated circuit.

11. The biological analysis apparatus according to claim 1, wherein the non-transitory memory comprises an electronic memory circuit.

12. The biological analysis apparatus according to claim 11, wherein the electronic memory circuit comprises at least one of Static Random Memory (SRAM) and Dynamic Random Access Memory (DRAM).

13. The biological analysis apparatus according to claim 1, wherein in each of the plural sensing and stimulation cells the pair of electric field applying electrodes has a third electrode and the pair of sensing electrodes has a fourth electrode, the third and fourth electrodes being structurally one electrode whereby the sensing and stimulation cell performs single ended sensing.

14. The biological analysis apparatus according to claim 1, wherein in each of the plural sensing and stimulation cells the pair of electric field applying electrodes has a third electrode and the pair of sensing electrodes has a fourth electrode, the third and fourth electrodes being structurally separate electrodes whereby the sensing and stimulation cell has no electrodes in common and thereby performs differential sensing.

15. The biological analysis apparatus according to claim 1, wherein comparing each applied electric field with the respective sensed electric field comprises cross-correlation of the applied electric field and the respective sensed electric field.

16. The biological analysis apparatus according to claim 1, wherein each of the plural sensing and stimulation cells has first and second states, the control apparatus controlling the sensing and stimulation cell to make a selection between the first and second states, the control apparatus controlling the electric field source circuit to apply the electric field to the biological particle when in the first state, and the sensing circuit sensing the sensed electric field corresponding to the applied electric field when in the second state.

17. The biological analysis apparatus according to claim 16, wherein each of the plural sensing and stimulation cells comprises at least one memory bit and at least one multiplexer, the at least one multiplexer controlled by the control apparatus to make the selection between the first and second states, and the at least one memory bit coupled to the at least one multiplexer to provide for persistence of the selected one of the first and second states.

* * * * *